(12) United States Patent
Vinu et al.

(10) Patent No.: US 8,361,203 B2
(45) Date of Patent: Jan. 29, 2013

(54) CARBON POROUS BODY AND ADSORBENT USING THE SAME

(75) Inventors: Ajayan Vinu, Tsukuba (JP); Katsuhiko Ariga, Tsukuba (JP); Masahiko Miyahara, Tsukuba (JP); Toshiyuki Mori, Tsukuba (JP)

(73) Assignee: National Institute for Materials Science, Tsukuba-Shi (JP)

( * ) Notice: Subject to any disclaimer, the term of this patent is extended or adjusted under 35 U.S.C. 154(b) by 0 days.

(21) Appl. No.: 13/427,087

(22) Filed: Mar. 22, 2012

(65) Prior Publication Data

US 2012/0178618 A1 Jul. 12, 2012

Related U.S. Application Data

(62) Division of application No. 11/883,179, filed as application No. PCT/JP2006/301596 on Jan. 25, 2006, now abandoned.

(30) Foreign Application Priority Data

Jan. 28, 2005 (JP) .................................. 2005-022234

(51) Int. Cl.
*B01D 53/02* (2006.01)

(52) U.S. Cl. .............................. 96/108; 95/900; 502/416

(58) Field of Classification Search .................... 96/108; 95/90; 264/29.1; 428/220, 299.1, 304.4; 502/108, 416
See application file for complete search history.

(56) References Cited

U.S. PATENT DOCUMENTS

| 4,514,346 | A | * | 4/1985 | Luhleich et al. ............. 264/29.5 |
| 4,580,404 | A | * | 4/1986 | Pez et al. ....................... 62/55.5 |
| 5,395,589 | A | * | 3/1995 | Nacson ........................... 422/88 |
| 5,785,741 | A | * | 7/1998 | Li et al. ............................. 96/4 |
| 6,812,187 | B1 | * | 11/2004 | Pak et al. ....................... 502/180 |
| 2005/0036935 | A1 | * | 2/2005 | Pak et al. .................. 423/445 R |
| 2005/0247202 | A1 | * | 11/2005 | Seki ................................ 96/146 |

\* cited by examiner

*Primary Examiner* — Duane Smith
*Assistant Examiner* — Christopher P Jones
(74) *Attorney, Agent, or Firm* — Manabu Kanesaka

(57) ABSTRACT

A carbon porous body (ICY) includes a carbon skeleton containing carbon atoms, wherein the carbon skeleton includes carbon main sections and carbon linking sections mutually linking the carbon main sections; a distance $D_1$ between adjacent carbon main sections and a distance $D_2$ between adjacent carbon linking sections satisfy the relationship of $D_1<D_2$; the carbon main sections are arranged three-dimensionally, regularly and symmetrically; and a specific surface area of the carbon porous body is not less than 1,300 $m^2/g$ and/or the pore capacity of the carbon porous body is not less than 1.5 $cm^3/g$.

4 Claims, 6 Drawing Sheets

Prior Art

CARBON POROUS BODY AND ADSORBENT USING THE SAME

CROSS-REFERENCE TO RELATED APPLICATION

This is a divisional application of Ser. No. 11/883,179 filed on Jul. 27, 2007 now abandoned, which is a national stage entry of PCT/JP2006/301596 filed on Jan. 25, 2006, which claims the priority of Japanese Patent Application No. 2005-022234 filed on Jan. 28, 2005, the content of which is incorporated.

TECHNICAL FIELD

The present invention relates to a carbon porous body. More particularly, the present invention relates to a carbon porous body that is stable relative to heat and water and has a large pore capacity and a large specific surface area, and an adsorbent using the same.

BACKGROUND ART

Research efforts have been and being made on porous materials for the purpose of adsorption and removal of harmful substances, adsorption and collection of useful substances and fixation of biological substances. Particularly, carbon porous bodies (meso porous carbon) that are stable under hydrothermal conditions (e.g. in hot water) are attracting attention. Techniques for manufacturing such carbon porous bodies by means of molds have been proposed (see, inter alia, Patent Document 1).

FIG. 12 of the accompanying drawings is a flowchart of a known method of manufacturing a carbon molecular body. This manufacturing method will be described below on a step by step basis.

Step S1210: A mold having gas holes (air holes) (meso porous silica) is impregnated with a mixture containing a silica oligomer, a carbon precursor substance that is a carbon-containing compound liable to be subjected to condensation polymerization and a liquid carrier. The mold has a structure where gas holes are irregularly three-dimensionally linked to each other or a structure where medium gas holes are linked to micro gas holes. The carbon precursor substance is a carbohydrate or a monomer. The silica oligomer is contained in order to raise the gas hole ratio in the obtained carbon molecular body. The liquid carrier accelerates the impregnation of the mixture to the mold.

Step S1220: The carbon precursor substance contained in the mixture with which the mold is impregnated is polymerized. The polymerization is realized by means of a heat treatment to produce a carbon precursor substance polymer that is formed in the gas holes of the mold. The liquid carrier is dried by the heat treatment.

Step S1230: The carbon precursor substance polymer formed in the gas holes is pyrolyzed and carbonized. The remaining liquid carrier is also removed by the pyrolysis.

Step S1240: The mold and the silica oligomer are treated by a solution that selectively dissolves them and removed. As a result, a carbon molecular body having micro gas holes is obtained.

REFERENCE DOCUMENT

Patent Document 1: JP 2004-244311-A

DISCLOSURE OF INVENTION

Problem to be Solved by the Invention

However, while the carbon molecular porous body (carbon porous body) obtained by the technique described in the Patent Document 1 can be made to contain a large number of micro gas holes by using a silica oligomer in order to produce a large specific surface area, the capacity of the pores (gas holes) is limited (and typically not greater than 1.7 cm$^3$/g). In other words, the size of a substance that the carbon porous body can adsorb is limited and the carbon porous body may not be able to adsorb a desired substance. Due to the structure of the mold (replica) used in the Patent Document 1, the obtained carbon porous body shows a structure produced by agglomeration of rod structures (e.g., a hexagonal structure), which is disadvantageous to the diffusion of the adsorbed substance into the inside of the carbon porous body. Therefore, it is an object of the present invention to provide a carbon porous body having a larger pore capacity and a larger specific surface area that can advantageously diffuse the substance it adsorbs into the inside and a method of manufacturing such a carbon porous body. Another object of the present invention is to provide applications (an adsorbent and a biomolecular element) using a carbon porous body as described above.

Means for Solving the Problem

In an aspect of the present invention, the above first object is achieved by providing a method of manufacturing a carbon porous body (ICY), characterized by comprising: a step of mixing a cage-shaped silica porous body and a carbon source, the cage-shaped silica porous body containing a silica skeleton, a plurality of pores formed by the silica skeleton and a plurality of channels also formed by the silica skeleton to mutually link the plurality of pores, the plurality of pores being arranged three-dimensionally, regularly and symmetrically, a diameter $d_1$ of the plurality of pores and a diameter $d_2$ of the plurality of channels satisfying the relationship of $d_1 > d_2$, the cage-shaped silica porous body and the carbon source being mixed so as to make the mol ratio (C/Si) of the silicon (Si) in the cage-shaped silica porous body and the carbon (C) in the carbon source satisfy the relationship of $0.8 < C/Si < 3.0$; a step of heating the mixture obtained by the mixing step; and a step of removing the cage-shaped silica porous body from the reaction product obtained from the heating step.

The cage-shaped silica porous body may be KIT-5.

A specific surface area s of the KIT-5 may be $450 < s$ (m$^2$/g) $< 690$.

The distance $d_2$ of the KIT-5 may be $4 < d_2$ (nm) $< 6$.
The distance $d_1$ of the KIT-5 may be $10 < d_1$ (nm) $< 14$.

The carbon source may satisfy the chemical formula of $C_lH_mO_n$ (where l is a positive integer and each of m and n is 0 or a positive integer).

The carbon source that satisfies the chemical formula of $C_lH_mO_n$ may be selected from a group of sugars, alcohols, aldehydes, ketones, carboxylic acids, ethers and hydrocarbons.

The sugars may be cane sugar and grape sugar.
The alcohols may be a group of octanol, hexanediol and benzyl alcohol.
The aldehydes may be acetaldehyde and butylaldehyde.
The ketones may be dibutyl ketone and cyclohexanone.
The carboxylic acids may be butyric acid and valeric acid.
The ethers may be dibutyl ether and dioxane.

The hydrocarbons may be a group of dodecane, adamantane and naphthalene.

The mol ratio (C/Si) of the silicon (Si) in the cage-shaped silica porous body and the carbon (C) in the carbon source may satisfy the relationship of $0.85 \leq C/Si \leq 0.95$.

The heating step may include a step of polymerizing the mixture at a first temperature and a step of carbonizing the mixture at a second temperature higher than the first temperature.

The mixture may be heated in the atmosphere at the first temperature selected from the temperature range between 70° C. and 150° C. for 5 to 8 hours in the polymerizing step.

The mixture may be heated further in the atmosphere at a temperature selected from the temperature range between 140° C. and 160° C. for 5 to 8 hours in the polymerizing step.

The mixture may be heated in a nitrogen atmosphere or in an inert gas atmosphere at the second temperature selected from the temperature range between 700° C. and 900° C. for 4 to 8 hours in the carbonizing step.

The reaction product may be filtered by means of hydrofluoric acid or an alkali aqueous solution in the removing step.

A method according to the present invention may further comprise a step of washing and drying the reaction product after the removing step.

In another aspect of the present invention, there is provided a carbon porous body (ICY) comprising a carbon skeleton containing carbon atoms, characterized in that the carbon skeleton includes carbon main sections and carbon linking sections mutually linking the carbon main sections, that a distance $D_1$ between adjacent carbon main sections and a distance $D_2$ between adjacent carbon linking sections satisfy the relationship of $D_1 < D_2$, that the carbon main sections are arranged three-dimensionally, regularly and symmetrically and that a specific surface area of the carbon porous body is not less than 1,300 m$^2$/g and/or the pore capacity of the carbon porous body is not less than 1.5 cm$^3$/g.

The distance $D_1$ and the distance $D_2$ may be respectively $4 \leq D_1$ (nm) $\leq 6$ and $9 \leq D_2$ (nm) $\leq 15$.

The carbon main sections may be arranged to form a face-centered cube.

The specific surface area of the carbon porous body may be not less than 1,600 m$^2$/g and/or the pore capacity of the carbon porous body may be not less than 2.0 cm$^3$/g.

In still another aspect of the present invention, there is provided an adsorbent comprising a carbon porous body (ICY) including a carbon skeleton containing carbon atoms, characterized in that the carbon skeleton includes carbon main sections and carbon linking sections mutually linking the carbon main sections, that a distance $D_1$ between adjacent carbon main sections and a distance $D_2$ between adjacent carbon linking sections satisfy the relationship of $D_1 < D_2$ that the carbon main sections are arranged three-dimensionally, regularly and symmetrically and that the specific surface area of the carbon porous body is not less than 1,300 m$^2$/g and/or the pore capacity of the carbon porous body is not less than 1.5 cm$^3$/g.

The distance $D_1$ and the distance $D_2$ may be respectively $4 \leq D_1$ (nm) $\leq 6$ and $9 \leq D_2$ (nm) $\leq 15$.

The carbon main sections may be arranged to form a face-centered cube.

The specific surface area of the carbon porous body may be not less than 1,600 m$^2$/g and/or the pore capacity of the carbon porous body may be not less than 2.0 cm$^3$/g.

In a further aspect of the present invention, there is provided a biomolecular element comprising a carbon porous body (ICY) including a carbon skeleton containing carbon atoms and biomolecules fixed to the carbon porous body, characterized in that the carbon skeleton includes carbon main sections and carbon linking sections mutually linking the carbon main sections, that a distance $D_1$ between adjacent carbon main sections and a distance $D_2$ between adjacent carbon linking sections satisfy the relationship of $D_1 < D_2$ that the carbon main sections are arranged three-dimensionally, regularly and symmetrically, that the specific surface area of the carbon porous body is not less than 1,300 m$^2$/g and/or the pore capacity of the carbon porous body is not less than 1.5 cm$^3$/g, that the biomolecules are fixed to the inside of the pores formed by the carbon main sections and the carbon linking sections and that the biomolecules are adapted to react with a predetermined substance.

The distance $D_1$ and the distance $D_2$ may be respectively $4 \leq D_1$ (nm) $\leq 6$ and $9 \leq D_2$ (nm) $\leq 15$.

The biomolecules may be selected from a group of proteins, nucleic acids and polysaccharides.

The predetermined substance may be a protein.

The protein may be an enzyme.

The enzyme may be lysozyme.

The carbon main sections may be arranged to form a face-centered cube.

The specific surface area of the carbon porous body may be not less than 1,600 m$^2$/g and/or the pore capacity of the carbon porous body may be not less than 2.0 cm$^3$/g.

ADVANTAGES OF THE INVENTION

A manufacturing method according to the present invention employs a cage-shaped silica porous body containing a plurality of pores arranged three-dimensionally, regularly and symmetrically as replica. Since such a cage-shaped silica porous body has a specific surface area and a pore capacity respectively smaller than the specific surface area and the pore capacity of any known replica, the obtained carbon porous body can be made to have a specific surface area and a pore capacity greater than those of any known carbon porous body. Additionally, since such a cage-shaped silica porous body and a carbon source are mixed to satisfy a predetermined mol ratio (namely 0.8<C/Si<3.0), it is possible to obtain a highly regular carbon porous body that is free from conglutination of carbon. A carbon porous body obtained in this way can show an improved adsorbing force than ever and adsorb a large substance that a conventional carbon porous body cannot adsorb. Additionally, it is possible to diffuse the adsorbed substance into the inside of the carbon porous body.

EXPLANATION OF REFERENCE SYMBOLS

Figure 1:
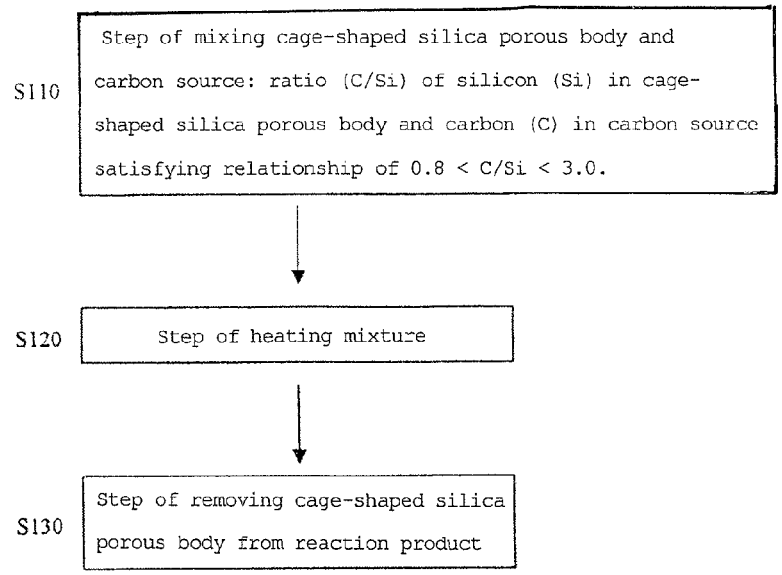
FIG. 1 is a flowchart of a method of manufacturing a carbon porous body (ICY) according to the present invention.

200: cage-shaped silica porous body
210: silica skeleton
220: pore
230: channel
300: carbon porous body (ICY)
310: carbon main section
320: carbon linking body
400: biomolecular element
410: biomolecular material

BEST MODE FOR CARRYING OUT THE INVENTION

Now, the present invention will be described in greater detail by referring to the accompanying drawings that illustrate preferred embodiments of the invention.

Embodiment 1

FIG. 1 is a flowchart of a method of manufacturing a carbon porous body (ICY) according to the present invention. The method will now be described below on a step by step basis.

Step S110: A cage-shaped silica porous body and a carbon source are mixed with each other. The mol ratio of the silicon (Si) in the cage-shaped silica porous body and the carbon (C) in the carbon source satisfies the relationship of $0.8<C/Si<3.0$.

Figure 2:
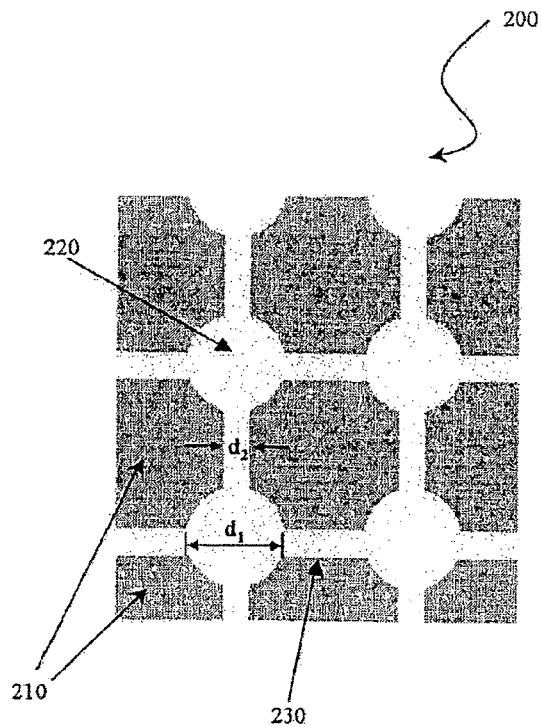
FIG. 2 is a schematic illustration of the structure of KIT-5.

FIG. 2 is a schematic illustration of the structure of KIT-5.

A structure 200 of KIT-5 is schematically illustrated as an example of cage-shaped silica porous body. The KIT-5 shown as an example of cage-shaped silica porous body includes a silica skeleton 210 made of silica, a plurality of pores 220 and a plurality of channels 230. The plurality of pores 220 and the plurality of channels 230 are formed by the silica skeleton 210.

The plurality of pores 220 are arranged three-dimensionally (although they are shown two-dimensionally in the drawing for the purpose of simplicity), regularly and symmetrically. The plurality of channels mutually link the plurality of pores 220. The diameter $d_1$ of the plurality of pores 220 and the diameter $d_2$ of the plurality of channels 230 satisfy the relationship of $d_1 > d_2$. Thus, the cage-shaped silica porous body has cage-shaped (birdcage-shaped) spaces in the inside and each space has such a structure that the inner diameter of the space is larger than that of the entrances thereof.

When KIT-5 is employed as cage-shaped silica porous body, the plurality of pores 220 show the symmetry of a face-centered cube Fm3m. The KIT-5 is manufactured typically by means of the technique described by Kleitz et al. in J. Phys. Chem. 107, 14296 (2003).

Note that the specific surface area, the lattice constant, the diameter $d_1$ and the diameter $d_2$ can vary remarkably depending on the manufacturing conditions (e.g., the baking temperature).

The specific surface area s (m²/g), the lattice constant $a_0$ (nm), the pore diameter $d_1$ (nm) and the channel diameter $d_2$ (nm) that are preferable for the purpose of the present invention are respectively $450<s$ (m²/g)$<690$, $17<a_0$ (nm)$<22$, $10<d_1$ (nm)$<14$ and $4<d_2$ (nm)$<6$.

Of the above-listed requirements, it is desirable that the requirement of the specific surface area s and that of the channel diameter $d_2$ are satisfied. This is because the KIT-5 does not operate as stable replica when the channel diameter $d_2$ is too small relative to the specific surface area s.

More preferably, the KIT-5 satisfies all the above-listed requirements.

Note that the structure of the obtained carbon porous body (ICY) depends on the structure of the selected cage-shaped silica porous body. Therefore, it is possible to obtain a carbon porous body having a desired profile, a desired pore diameter and a desired specific surface area by appropriately selecting a cage-shaped silica porous body.

Now, referring again to Step S110 in FIG. 1, the carbon source is a compound $C_l H_m O_n$ (where l is a positive integer and each of m and n is 0 or a positive integer) that is made of all or part of carbon, hydrogen and oxygen. Such a carbon source may be selected from a group of sugars, alcohols, aldehydes, ketones, carboxylic acids, ethers and hydrocarbons.

Preferably, the sugars are cane sugar and grape sugar. The alcohols may be a group of octanol, hexanediol and benzyl alcohol. The aldehydes may be acetaldehyde and butylaldehyde. The ketones may be dibutyl ketone and cyclohexanone. The carboxylic acids may be butyric acid and valeric acid. The ethers may be dibutyl ether and dioxane. The hydrocarbons may be a group of dodecane, adamantane and naphthalene. The carbon source may be formed by combining more than one of the above-listed materials. The carbon source is not limited to the above-listed materials.

A cage-shaped silica porous body to be used for the purpose of the present invention shows a specific surface area and a pore capacity smaller than those of any conventional silica porous body. Therefore, when a conventional method of manufacturing a carbon porous body is employed, there arises a problem that the carbon source is in short supply and hence carbon cannot be sufficiently filled into the cage-shaped silica porous body or a problem that carbon is excessively supplied and conglutination of carbon takes place after removing the cage-shaped silica porous body. Then, it is not possible to obtain a carbon porous body having a structure where pores are arranged regularly. In short, the ratio of the carbon source relative to the cage-shaped silica porous body is important. According to the present invention, the cage-shaped silica porous body and the carbon source are mixed in such a way that the mol ratio (C/Si) of the silicon (Si) in the cage-shaped silica porous body and the carbon (C) in the carbon source satisfies the relationship of $0.8<C/Si<3.0$.

It is possible to obtain a carbon porous body (ICY) having a structure where pores are arranged regularly when the mol ratio is within the above-defined range.

Preferably, the mol ratio satisfies the relationship of $0.85 \leq C/Si \leq 0.95$. It is possible to control the pore structure of the obtained carbon porous body (specifically in terms of the pore capacity, the surface area, the pore diameter (corresponding to distance $D_1$, which will be described hereinafter)

and the diameter of the internal cage spaces (corresponding to distance $D_2$, which will be described hereinafter)) by adjusting the mol ratio within the above-defined range.

Step S120: The mixture obtained in Step S110 is heated. As a result, the mixture gives rise to a chemical reaction to make it possible to obtain a carbon porous body. More particularly, the mixture is polymerized at a first temperature and subsequently carbonized at a second temperature that is higher than the first temperature.

The polymerization is realized by heating the mixture in the atmosphere at the first temperature selected from the temperature range between 70° C. and 150° C. for 5 to 8 hours. Any heating means such as an oven or a hot plate may be used for the heating. The carbon source is subjected to polymerization out of the mixture by the heating. Subsequently, the carbon source is placed in the pores of the cage-shaped silica porous body as the mixture is agitated. The polymerization may be conducted further by heating the mixture in the atmosphere at a temperature selected from the temperature range between 140° C. and 160° C. for 5 to 8 hours.

The carbonization is realized by heating the mixture in a nitrogen atmosphere or in an inert gas atmosphere at the second temperature selected from the temperature range between 700° C. and 900° C. for 4 to 8 hours. Any heating means such as an electric furnace may be used for the heating. The polymerized carbon source is carbonized by as a result of the heating. The reaction product obtained in the pores of the cage-shaped silica porous body is a carbon porous body (ICY).

The polymer obtained as a result of the polymerization may be dried and reduced to micro particles before the carbonization. Then, it is possible to reduce the time necessary for the carbonization.

Step S130: The cage-shaped silica porous body is removed from the reaction product obtained as a result of Step S120. It is possible to extract the ICY, or the reaction product, by filtering the cage-shaped silica porous body by means of hydrofluoric acid or an alkali aqueous solution. Any alkali aqueous solution that can dissolve a cage-shaped silica porous body may be used.

After Step S130, the extracted reaction product may be washed and dried. Pure water, distilled water or ethanol may be used for the washing. The extracted reaction product may be dried by any heating means such as an oven or a hot plate.

Thus, with a manufacturing method according to the present invention, it is possible to obtain a novel cage-shaped carbon porous body by means of a cage-shaped silica porous body where a plurality of pores are arranged three-dimensionally, regularly and symmetrically as replica.

Since the cage-shaped silica porous body has a specific surface area and a pore capacity respectively smaller than those of any conventional replica, the obtained carbon porous body has a specific surface area and a pore capacity respectively greater than those of any known carbon porous body.

Additionally, with a manufacturing method according to the present invention, it is possible to obtain a carbon porous body that is free from conglutination of carbon and shows a regularity that reflects the structure of the cage-shaped silica porous body because the cage-shaped silica porous body and the carbon source are mixed so as to satisfy the above described predetermined mol ratio.

Figure 3:
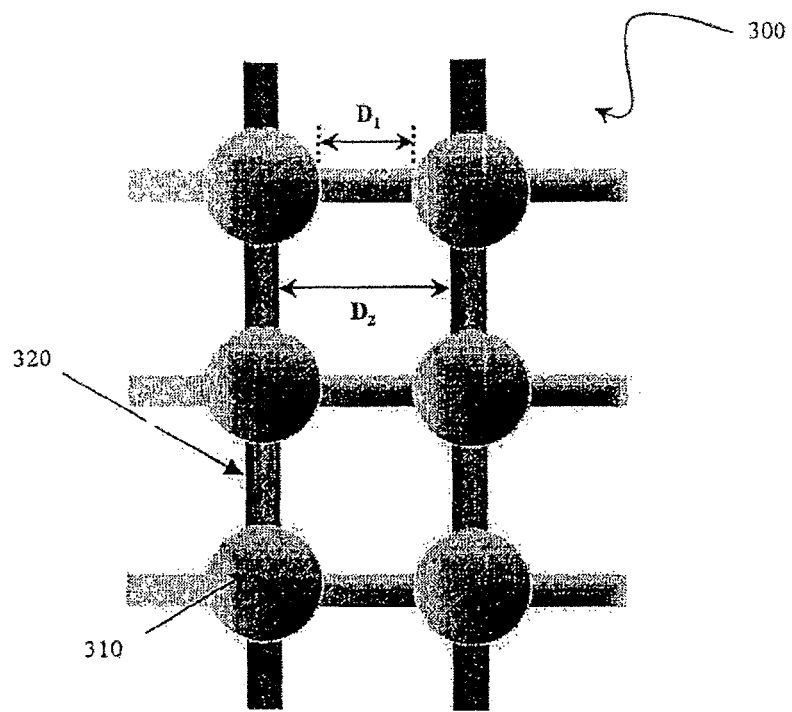
FIG. 3 is a schematic illustration of a carbon porous body (ICY) according to the present invention.

FIG. 3 is a schematic illustration of a carbon porous body (ICY) according to the present invention.

The carbon porous body (ICY) 300 illustrated in FIG. 3 is formed by using KIT-5 as cage-shaped silica porous body by means of a manufacturing method according to the present invention described above by referring to FIG. 1. It should be noted, however, that the structure of ICY 300 is not limited to the illustrated one.

A carbon porous body (ICY) 300 according to the present invention is formed by using a carbon skeleton. The ICY 300 includes carbon main sections 310 and carbon linking sections 320 mutually linking the carbon main sections 310. The carbon main sections 310 are arranged three-dimensionally (although they are shown two-dimensionally in the drawing for the purpose of simplicity), regularly and symmetrically. The distance $D_1$ between adjacent carbon main sections 310 and the distance $D_2$ between adjacent carbon linking sections 320 satisfy the relationship of $D_1<D_2$.

Thus, the ICY 300 has a structure where large spaces (separating the carbon linking sections 320) are linked by the parts (separating the carbon main sections 310) where the thick carbon skeleton forms narrow pores. Preferably, the carbon main sections 310 are arranged so as to form a face-centered cube. Preferably, the distance $D_1$ (nm) is not smaller than 4 nm and not greater than 6 nm. Preferably, the distance $D_2$ (nm) is not smaller than 9 nm and not greater than 15 nm.

Note that an ICY 300 having a specific surface area of not smaller than 1,300 $m^2/g$ and/or a pore capacity of not smaller than 1.5 $cm^3/g$ can be obtained by a method according to the present invention described above by referring to FIG. 1.

It is possible to obtain an ICY 300 having a specific surface area of not smaller than 1,600 $m^2/g$ and/or a pore capacity of not smaller than 2.0 $cm^3/g$ by appropriately selecting a cage-shaped silica porous body.

With an ICY 300 according to the present invention, it is possible to effectively fix (absorb) a greater substance such as a protein in the space having a cage diameter denoted by the distance $D_2$ if compared with the conventional art.

As described above by referring to FIG. 3, a cage-shaped silica porous body according to the present invention has narrow pores and large internal spaces to show a structure suitable for a catalytic reaction.

A carbon porous body according to the present invention can be utilized as a catalyst to be used as the anode or the cathode of a fuel cell. It is possible to improve the catalytic activity and the dispersion in the cell because a carbon porous body according to the present invention provides a large specific surface area and/or a large pore capacity if compared with the conventional art. Therefore, a carbon porous body according to the present invention can reduce the quantity of catalyst in the fuel cell and hence it is possible to downsize the cell.

Additionally, a carbon porous body according to the present invention can be utilized as an adsorbent. Particularly, different from a silica porous body, a carbon porous body is highly hydrophobic and can effectively operate to adsorb harmful substances having hydrophobic groups. Such harmful substances include PCB, environmental hormones that are endocrine disruptors and odorous substances.

Now, an application of a cage-shaped silica porous body according to the present invention as described above by referring to Embodiment 1 to a biomolecular element (biomolecule identifier) will be described below.

Embodiment 2

Figure 4:
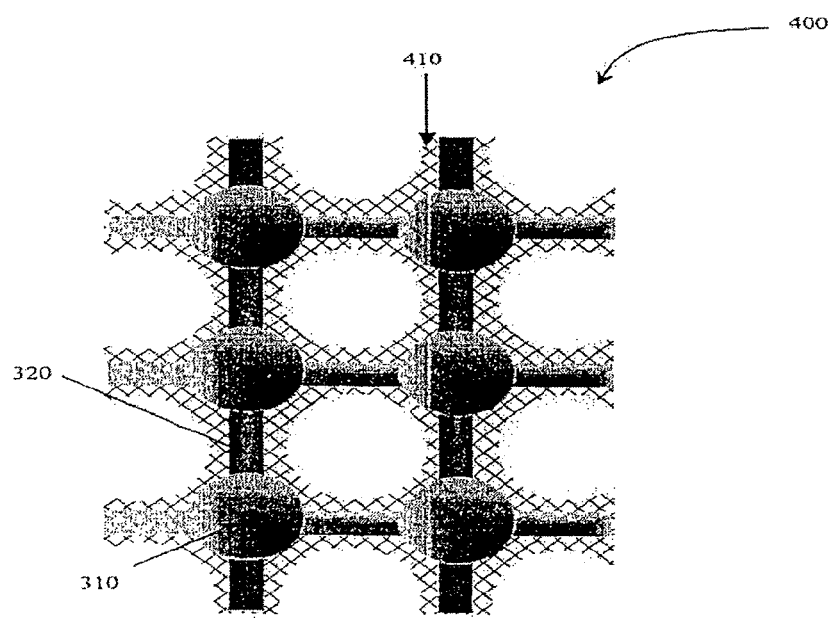
FIG. 4 is a schematic illustration of a biomolecular element according to the present invention.

FIG. 4 is a schematic illustration of a biomolecular element according to the present invention.

Biomolecular element 400 includes a cage-shaped silica porous body 300 and a biomolecular material 410 adsorbed to the inner wall surface of the cage-shaped silica porous body 300.

The biomolecular element 400 may be manufactured simply by fixing a biomolecular material to a cage-shaped silica porous body 300. A biomolecular material 410 may be a substance that selectively reacts on a specific substance (receptor), a substance that selectively takes a catalytic action on a specific substance or a substance that inactivates substances other than a specific substance.

The biomolecular material 410 may typically be selected from a group of proteins, nucleic acids and polysaccharides.

The above specific substance, or the biomolecular material 410, is a protein. More particularly, it is an enzyme. More particularly, it is lysozyme.

For the purpose of fixation of the biomolecular material 410, a cage-shaped silica porous body 300 according to the present invention is immersed into a solution where the biomolecular material 410 is dissolved. Then, the biomolecular material 410 in the solution is adsorbed by the cage-shaped silica porous body 300. The cage-shaped silica porous body 300 that adsorbs the biomolecular material may be appropriately dried to eliminate an unnecessary solvent.

The operation of the biomolecular element 400 obtained in the above-described manner will be described below.

The biomolecular element 400 may be used with a detection means (not shown). Any detection means may be used for the purpose of the present invention so long as it can display the fact that the biomolecular element 400 detects the specific substance by way of a change of electric current, voltage, quantity of light, mass, calorie or the like. If the biomolecular material 410 of the biomolecular element 400 can visualize such a change, the detection means may be omitted.

An object solution of examination is provided to the biomolecular element 400.

The object solution of examination passes through the biomolecular element 400 and discharged. If the object solution of examination contains a substance that reacts on the above described biomolecular material 410, the biomolecular material 410 reacts on the substance in the object solution of examination, takes a catalytic action on the substance, inactivates substances other than the specific substance or takes some other action.

A signal that indicates that the biomolecular element 400 detects a specific substance (and corresponds to a change of electric current, voltage, quantity of light, mass, calorie or the like) is notified to the detection means. The detection means can display that the specific substance exists in the object solution of examination according to the signal from the biomolecular element 400.

If the object solution of examination does not contain a substance that reacts on the above-described biomolecular material 410, the biomolecular material 410 notifies the detection means of a signal indicating that the biomolecular element 400 does not detect the specific substance (and corresponds to no change of electric current, voltage, quantity of light, mass, calorie or the like). The detection means can display that the specific substance does not exist in the object solution of examination according to the signal from the biomolecular element 400.

It is possible to detect several different substances at the same time by combining a plurality of biomolecular elements 400 where respective biomolecular materials 410 that react on different respective substances are fixed.

Now, the present invention will be described below by way of specific examples. However, it should be noted that the present invention is by no means limited to the examples.

Example 1

A carbon porous body was prepared by means of the manufacturing method according to the present invention that is described above by referring to FIG. 1. 1 g of KIT-5 prepared at 150° C. (to be referred to as KIT-5-150 hereinafter) and selected as cage-shaped silica porous body and 0.75 g of cane sugar selected as carbon source were brought in and mixed with 0.8 g of concentrated sulfuric acid and 2.5 g of water. The mol ratio of the silicon (Si) in the silica porous body and the carbon (C) in the carbon source was C/Si=1.5. Thereafter, the mixture was heated in the atmosphere in an oven at 100° C. for 6 hours. Then, the temperature was raised to 160° C. and held to that temperature for six hours to complete polymerization. The obtained polymer was held to 877° C. in a nitrogen flow of 50 ml/min for carbonization. The KIT-5-150 was removed by means of 5 wt % hydrofluoric acid and subsequently the reaction product ICY (to be referred to as ICY-1 hereinafter) was washed with ethanol several times and then dried at 120° C.

The obtained reaction product ICY-1 was analyzed for structure by means of an X-ray diffractometer (Siemens D5005, Brucker AXS, UK). The operating conditions of the X-ray diffractometer included the use of Cu—K$\alpha$ rays, 40 kV/50 mA and a scanning rate of 0.5° 2$\theta$/min. The X-ray diffraction pattern of the used KIT-5-150 and that of the ICY-1 were compared.

The ICY-1 was observed through high resolution transmission type electron microscopes (JEOL-3000 and JEOL-3100-FEF, JEOL Ltd., Japan). The specimen was regulated by granulating it by means of a mortar and dispersing the granules on a carbon film perforated at positions located above a Cu-made lattice. The operating conditions of the transmission type electron microscopes included an acceleration voltage of 300 kV and a resolution of 150,000 to 1,200,000 times.

The nitrogen adsorption-desorption isotherms of the specimen were observed by means of a specific surface area and pore size distribution measuring instrument (Autosorb 1, Quantachrome, USA). The ICY-1 was deaerated at 523K under pressure not higher than 10-5hPa for 3 hours and subsequently observed at 77K. The presence or absence of pores and, if present, the profiles of the pores can be found by observing the absorption-desorption isotherms. Some of the results of the above analysis and observation are illustrated in FIGS. 5 through 9 and will be described below in detail.

Example 2

ICY was prepared in this example under the same preparing conditions by following the same preparation process as in Example 1 except that KIT-5 prepared at 130° C. was used as cage-shaped silica porous body (to be referred to as KIT-5-130 hereinafter).

Figure 5:
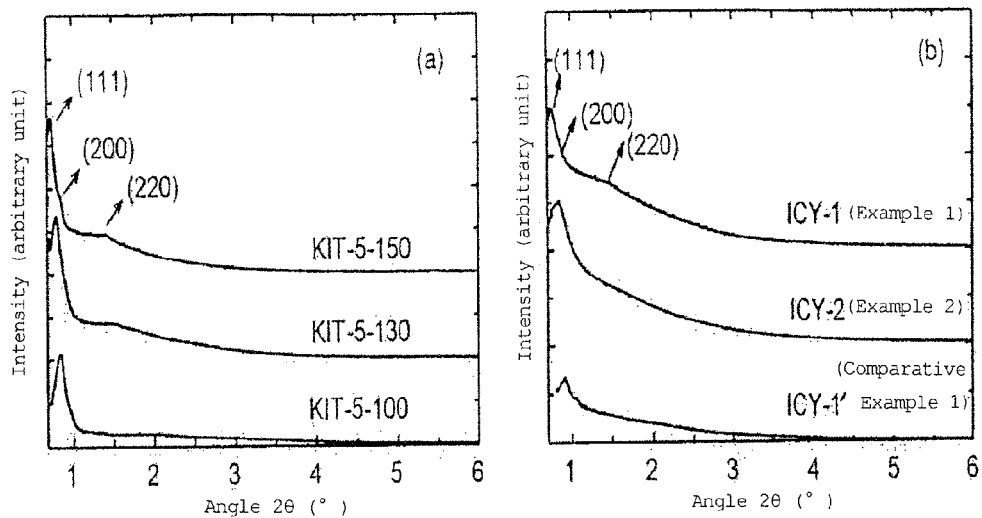
FIG. 5(a) is a graph illustrating the X-ray diffraction patterns of cage-shaped silica porous bodies KIT-5s (KIT-5-150, KIT-5-130 and KIT-5-100) calcined at different temperatures.
FIG. 5(b) is a graph illustrating the X-ray diffraction patterns of ICYs (ICY-1, ICY-2 and ICY-1')
Figure 6:
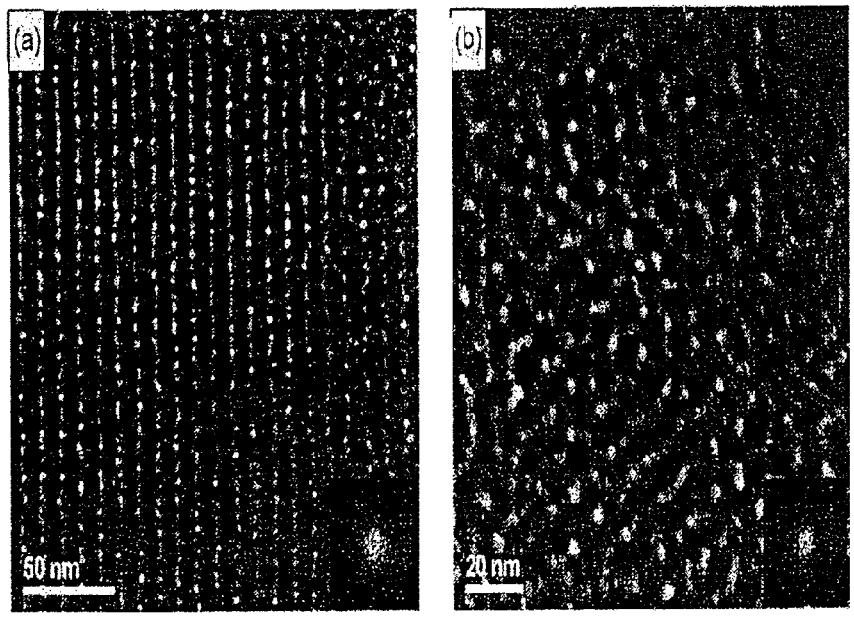
FIG. 6(a) is a microscopic photograph of ICY-1 taken along a surface parallel to the air holes thereof.
FIG. 6(b) is a microscopic photograph of ICY-1 showing a cross section thereof.
Figure 7:
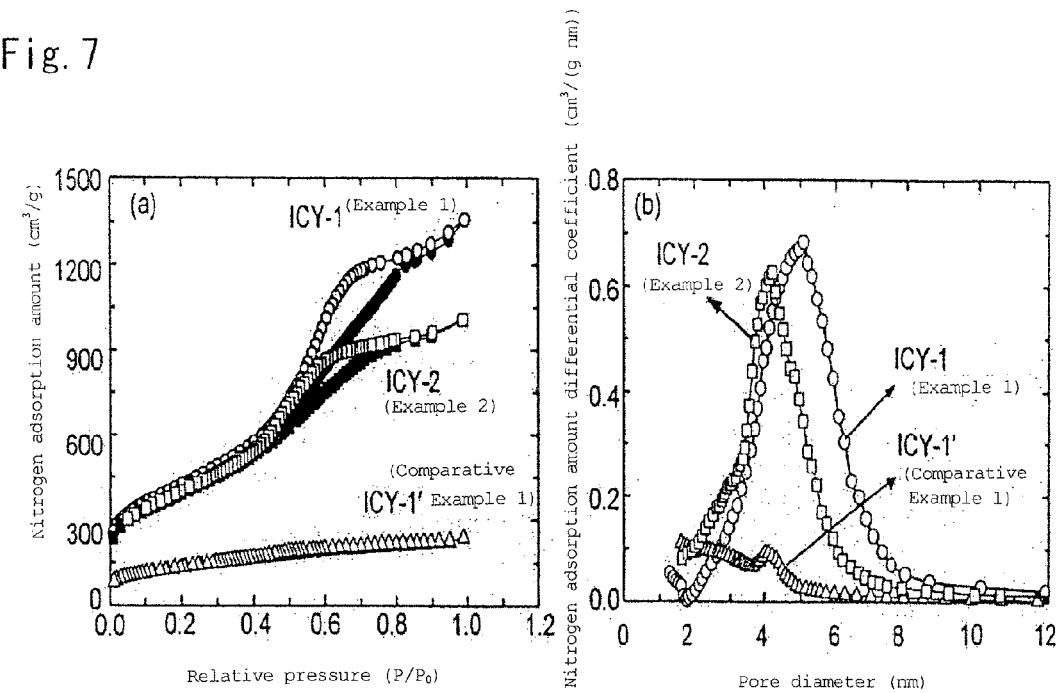
FIG. 7(a) is a graph illustrating the nitrogen adsorption-desorption isotherms of ICY-1, ICY-2 and ICY-1'.
FIG. 7(b) is a graph illustrating the pore distributions of ICY-1, ICY-2 and ICY-1'.

The obtained reaction product ICY (to be referred to as ICY-2 hereinafter) was analyzed for structure by means of an X-ray diffractometer and observed for nitrogen adsorption-desorption isotherms by means of a specific surface area and pore distribution measuring instrument as in Example 1. Some of the results of the above analysis and observation are illustrated in FIGS. 5 and 7 and will be described below in detail.

Comparative Example 1

ICY was prepared in this comparative example under the same preparing conditions by following the same preparation process as in Example 1 except that KIT-5 prepared at 100° C. was used as cage-shaped silica porous body (to be referred to as KIT-5-100 hereinafter). The obtained reaction product ICY (to be referred to as ICY-1' hereinafter) was analyzed for structure by means of an X-ray diffractometer and observed for nitrogen adsorption-desorption isotherms by means of a specific surface area and pore distribution measuring instrument. Some of the results of the above analysis and observation are illustrated in FIGS. 5 and 7 and will be described below in detail.

Example 3

The process of Example 1 was followed except that 0.45 g of cane sugar was used as carbon source and hence the process of this example will not be described here any further. The ratio of the silicon (Si) in the silica porous body and the carbon (C) in the carbon source showed a relationship of C/Si=0.9. The reaction product ICY (to be referred to as ICY-3 hereinafter) obtained in this Example 3 was analyzed for structure by means of an X-ray diffractometer and observed for nitrogen adsorption-desorption isotherms by means of a specific surface area and pore distribution measuring instrument.

Then, the protein (lysozyme) adsorption characteristic of the ICY-3 was observed. 20 mg of ICY-3 was dispersed in 4 g of a lysozyme buffer aqueous solution (with a concentration within a range between 17 μmol/L and 280 μmol/L) with pH 11. The dispersion liquid was agitated at a rate of 160 turns per minute for about 96 hours at 20° C. After getting to an adsorption equilibrium, the ultraviolet absorption (281.5 nm) of the supernatant liquid was observed by means of an ultraviolet-visible spectrometer (Shimadzu UV-3150, Shimadzu Corporation Japan). For the purpose of reference, the adsorption characteristic of a known carbon porous body CMK and that of the ICY-3 were compared.

Additionally, the infrared absorption spectrum of the protein that was adsorbed by the ICY-3 was observed before and after the adsorption of the protein by means of a Fourier transform infrared spectrometer (Nicolet Nexus 670, Thermo Electron, USA) in order to see the stability of the protein. The observation wavelength range was 400 cm$^{-1}$ through 950 cm$^{-1}$. Some of the results of the above analysis and observation are illustrated in FIGS. 8 through 11 and will be described below in detail.

Example 4

The process of Example 1 was followed except that 1.2 g of cane sugar was used as carbon source and hence the process of this example will not be described here any further. The ratio of the silicon (Si) in the silica porous body and the carbon (C) in the carbon source showed a relationship of C/Si=2.4. The reaction product ICY (to be referred to as ICY-4 hereinafter) obtained in this Example 4 was analyzed for structure by means of an X-ray diffractometer and observed for nitrogen adsorption-desorption isotherms by means of a specific surface area and pore distribution measuring instrument and also for lysozyme adsorption characteristic by means of an ultraviolet-visible spectrometer. Some of the results of the above analysis and observation are illustrated in FIGS. 8 through 11 and will be described below in detail.

Comparative Example 2

Figure 8:
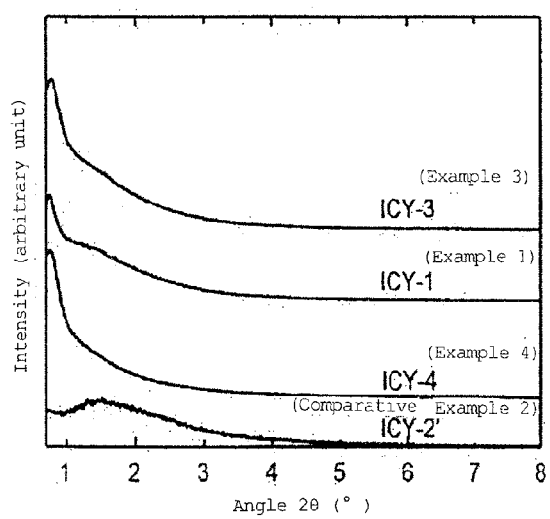
FIG. 8 is a graph illustrating the X-ray diffraction patterns of ICY-1, ICY-3, ICY-4 and ICY-2'.
Figure 9:
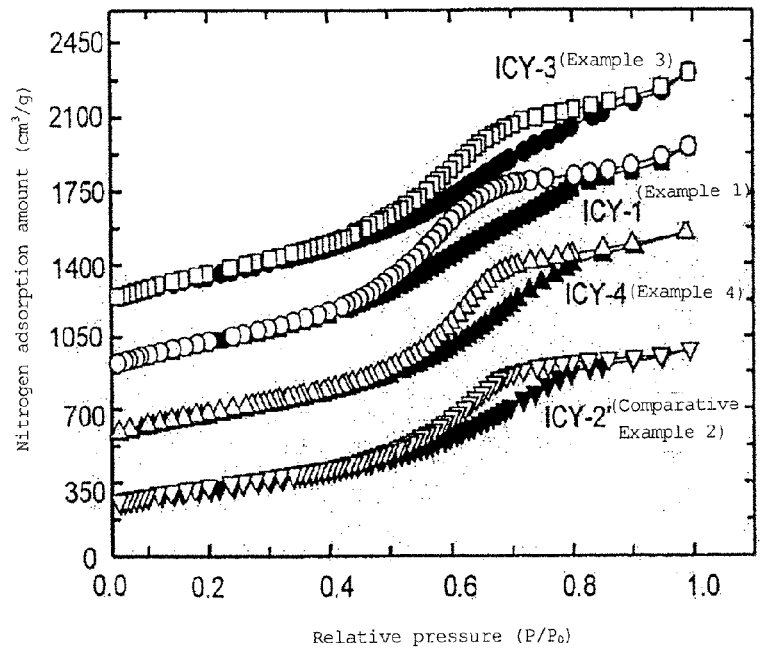
FIG. 9 is a graph illustrating the nitrogen adsorption-desorption isotherms of ICY-1, ICY-3, ICY-4 and ICY-2'.

The process of Example 1 was followed except that 2.0 g of cane sugar was used as carbon source and hence the process of this example will not be described here any further. The ratio of the silicon (Si) in the silica porous body and the carbon (C) in the carbon source showed a relationship of C/Si=4.0. The reaction product ICY (to be referred to as ICY-2' hereinafter) obtained in this Comparative Example 2 was analyzed for structure by means of an X-ray diffractometer and observed for nitrogen adsorption-desorption isotherms by means of a specific surface area and pore distribution measuring instrument. Some of the results of the above analysis and observation are illustrated in FIGS. 8 and 9 and will be described below in detail.

FIG. 5A is a graph illustrating the X-ray diffraction patterns of cage-shaped silica porous bodies KIT-5s (KIT-5-150, KIT-5-130 and KIT-5-100). FIG. 5B is a graph illustrating the X-ray diffraction patterns of ICYs (ICY-1, ICY-2 and ICY-1').

As shown in FIG. 5A, it was confirmed that all the KIT-5s including the KIT-5-150 having a baking temperature of 150° C. that was used in Examples 1, 3 and 4 and Comparative Example 2, the KIT-5-130 having a baking temperature of 130° C. that was used in Example 2 and the KIT-5-100 having a baking temperature of 100° C. that was used in Comparative Example 1 showed peaks that correspond to diffractions of (111), (200) and (220) of the face-centered cubic lattice (space group Fm3m) within the range of 2θ=between 0.7 and 3. The diffraction peaks were shifted to the low angle side and the diffraction intensity was increased as the baking temperature rose.

The lattice constants $a_0$ were determined from the diffraction peak (111). Table 1 below shows the obtained results. As shown in Table 1, the lattice constants $a_0$ of KIT-5-100, KIT-5-130 and KIT-5-150 are 18.1 nm, 19.0 nm and 20.7 nm respectively. Thus, it was found that the lattice constant $a_0$ is increased as the baking temperature is raised. The specific surface area, the pore capacity, the pore diameter $d_1$ (which corresponds to the diameter $d_1$ in FIG. 2) and the diameter $d_2$ (which corresponds to the diameter $d_2$ in FIG. 2) of each of the KIT-5s used in the examples were also looked into. The obtained results are also shown in Table 1.

TABLE 1

| KIT-5 | baking temperature (° C.) | lattice constant $a_0$ (nm) | specific surface area s (m$^2$/g) | pore capacity v (cm$^3$/g) | diameter $d_1$ (nm) | channel diameter $d_2$ (nm) |
|---|---|---|---|---|---|---|
| KIT-5-100 | 100 | 18.1 | 701 | 0.44 | 10.8 | 3.8 |
| KIT-5-130 | 130 | 19.0 | 675 | 0.69 | 12.3 | 4.3 |
| KIT-5-150 | 150 | 20.7 | 470 | 0.75 | 13.5 | 5.7 |

As seen from Table 1, it was found that, as the baking temperature rises, micro pores are removed to decrease the specific surface while the value of $d_1$ and that of $d_2$ increase to raise the pore capacity. Note that the structural difference among the KIT-5s is also produced by detailed baking conditions (the rate of temperature rise, the baking atmosphere, the baking time, etc.)

As shown in FIG. 5B, the peaks that are similar to those of the diffraction pattern of FIG. 5A and correspond to the diffractions of (111), (200) and (220) of the face-centered cubic lattice (space group Fm3m) were also confirmed. However, all the peaks are rather broad and the diffraction intensity was reduced. As in the case of KIT-5, the diffraction peaks were shifted and the diffraction intensity was changed depending on the KIT-5 that was used for the ICY. The lattice constants $a_0$ were determined from the diffraction peak (111) in the same manner. The obtained results are shown in Table 2. The diffraction constants $a_0$ of ICY-1, ICY-2 and ICY-1' were 20.68 nm, 18.2 nm and 16.8 nm respectively. It was found that they showed values similar to the lattice constants of the KIT-5s that were respectively used for them. This fact indicates that each of the carbon porous bodies maintained the regular structure of the replica, or the cage-shaped silica porous body (KIT-5 in the corresponding example), after removing the replica.

Each of the ICYs was subjected to a thermogravimetric analysis in an oxygen atmosphere in order to confirm that the diffraction patterns shown in FIG. 5B are not produced by the remaining KIT-5. As a result, it was found that the residual KIT-5 is about 1 wt % to 1.5 wt % for all the carbon porous bodies including ICY-1, ICY-2 and ICY-1'. Thus, it was confirmed that the X-ray diffraction patterns in FIG. 5B are not produced by the residual KIT-5s.

From above, it was found the lattice constants of ICYs vary as a function of the KIT-5s used for obtaining them. To be more specific, it was found that an ICY having a large lattice constant can be obtained by selecting a KIT-5 showing a large lattice constant $a_0$. The preferable range of lattice constant $a_0$ of KIT-5 is $17<a_0$ (nm)$<22$.

FIG. 6A is a microscopic photograph of ICY-1 taken along a surface parallel to the air holes thereof. FIG. 6B is a microscopic photograph of ICY-1 showing a cross section thereof. In FIGS. 6A and 6B, the light stripes indicate pore walls (e.g., 310 or 320 in FIG. 3), whereas dark stripes indicate pores (e.g., spaces indicated by distance $D_2$ in FIG. 3). Thus, it was found from FIGS. 6A and 6B that the obtained ICY-1 had a highly regular structure and a micro pore distribution.

Light spots (like the enlarged ones at corners of FIGS. 6A and 6B) are arranged regularly in the images illustrated in FIGS. 6A and 6B to prove that ICY-1 had a cage-shaped porous structure. While similar microscopic images were obtained for ICY-2, no such regularity was observed in the images of ICY-1' because pores had been crushed there. This is because KIT-5-100 does not function stably as replica due to the micro pores remaining in the inside when KIT-5-100 baked at a relatively low temperature is employed.

FIG. 7A is a graph illustrating the nitrogen adsorption-desorption isotherms of ICY-1, ICY-2 and ICY-1' and FIG. 7B is a graph illustrating the pore distributions of ICY-1, ICY-2 and ICY-1'. As seen from FIG. 7A, the nitrogen adsorption-desorption isotherms of ICY-1 and those of ICY-2 showed the H2 type (the IV type in the IUPAC classification) hysteresis. This fact means that meso pores (pores having a diameter of 2 to 50 nm) existed in ICY-1 and ICY-2 and nitrogen adsorption that is attributable to capillary condensation took place under relative pressure of 0.5 to 0.8.

On the other hand, the nitrogen adsorption-desorption isotherms of ICY-1' was of the II type (in the IUPAC classification) and did not show any hysteresis. This fact means that no pores were found or micro pores (pores having a diameter not greater than 2 nm) existed in ICY-1', leading to the fact that the nitrogen adsorption amount of ICY-1' was remarkably smaller than that of ICY-1 and that of ICY-2.

Subsequently, the specific surface area and the pore capacity of ICY-1, those of ICY-2 and those of ICY-1' were determined by means of the BET formula, using the nitrogen adsorption-desorption isotherms of FIG. 7A. Table 2 shows the obtained results.

The specific surface area and the pore capacity of ICY-1' were respectively not greater than 500 m²/g and not greater than 0.4 cm³/g because ICY-1' did not have any pores or only micro pores existed there. However, it was found that both ICY-1 and ICY-2 had a specific surface area of not smaller than 1,400 m²/g and a pore capacity of not smaller than 1.5 cm³/g, which were relatively large, because they had meso pores in the inside. Particularly, ICY-1 showed a large pore capacity of not smaller than 2.0 cm³/g, which is by far greater than that of any conventional carbon porous body, and hence could be advantageous for the purpose of adsorption (fixation) of a substance having a large structure such as biomolecules. Referring again to Tables 1 and 2, it was found that an ICY having a large specific surface area can be obtained by using a KIT-5 having a small specific surface area.

Accordingly, it was also found that an ICY having a large pore capacity can be obtained by using a KIT-5 having a large pore capacity. Preferably, the specific surface area of KIT-5 to be used for the purpose of the present invention satisfies a requirement of $450<s$ (m²/g)$<690$.

FIG. 7B is a graph illustrating the pore distributions determined respectively from the pore capacities of the ICYs as determined from the nitrogen adsorption/desorption isotherms of FIG. 7A. The determined pore diameter $D_1$ is similar to the distance $D_1$, which is described above by referring to FIG. 3. The obtained results are shown in Table 2.

From FIG. 7B, it was found that the pore diameter $D_1$ of ICY-1 was 5.2 nm and that of ICY-2 was 4.0 nm. On the other hand, ICY-1' did not show any clear pore distribution. From FIGS. 7A and 7B and a microscopic photograph (not shown), it was found that ICY-1' did not show any pores (except a small number of micro pores) and its structure had been partly broken down.

This is because the channel diameter of KIT-5-100 used for ICY-1' was too small relative to the specific surface area and hence KIT-5-100 did not stably function as replica as seen from Table 1. Thus, it is necessary to use a KIT-5 that has a preferable specific surface area as described above and satisfies the requirement for the channel diameter of $4<d_2$ (nm)$<6$ in order to reliably obtain an ICY having a stable structure as shown in FIG. 3.

Subsequently, the cage diameter $D_2$ (that corresponds to the distance $D_2$ in FIG. 3) was determined by means of formula (1) shown below from the pore diameter $D_1$.

$$D_2 = a_0 \times (6\epsilon/\pi v)^{1/3} \quad (1)$$

In the formula (1), $a_0$ is the lattice constant (nm) of ICY and s is the volume ratio of the pores, while v is the number of pores in a unit lattice (v=4 in the case of space group Fm3m). Table 2 also shows the obtained results.

The cage diameter $D_2$ of ICY-1 was 13.5 nm and that of ICY-2 was 12.3 nm. Thus, it is possible to obtain an ICY having a pore diameter $D_1$ and a cage diameter. $D_2$ that are feasible for practical applications (or respectively $4 \leq D_1$ (nm) $\leq 6$ and $9 \leq D_2$ (nm) $\leq 15$) by using a KIT-5 that satisfies the above-described requirements for the specific surface area and the channel diameter.

Thus, it was shown from Examples 1 and 2 and Comparative Example 1 that, when the mol ratio of the silicon (Si) in the silica porous body and the carbon (C) in the carbon source is constant (e.g., C/Si=1.5), it is important to select an appropriate replica in order to obtain an ICY that is stable and has a large specific surface area and a large pore capacity. Particularly, it is effective to use a replica showing a large lattice constant in order to obtain an ICY that has a large specific surface area, a large pore capacity and a large cage diameter. More specifically, it is desirable to use a KIT-5 that satisfies the requirement of $450<(m^2/g)<690$ for the specific surface area s and that of $4<d_2$ (nm)$<6$ for the channel diameter $d_2$.

FIG. 8 is a graph illustrating the X-ray diffraction patterns of ICY-1, ICY-3, ICY-4 and ICY-2'. As in the case of ICY-1 shown in FIG. 5B, an X-ray diffraction pattern showing peaks that correspond to diffractions of (111), (200) and (220) of the face-centered cubic lattice (space group Fm3m) within the range of 2θ=between 0.7 and 3 was confirmed for ICY-3 and also for ICY-4. No substantial shift of diffraction peaks was observed in the X-ray diffraction patterns. On the other hand, ICY-2' did not show any X-ray diffraction pattern of the face-centered lattice.

The lattice constants $a_0$ were determined from the diffraction peak (111).

Table 2 also shows the obtained results. As described above by referring to FIGS. 5A and 5B and Table 2, the lattice constant $a_0$ of the selected replica (KIT-5-150 here) was 20.7 nm. The lattice constants of ICY-1, ICY-3 and ICY-4 were respectively 20.68 nm, 19.98 nm and 19.48 nm, which are close to the lattice constant of KIT-5.

On the other hand, it was found that the lattice constant $a_0$ of ICY-2' was 7.03 nm and hence did not reflect the structure of KIT-5. From the above, the mol ratio of the silicon (Si) in the silica porous body and the carbon (C) in the carbon source is important to the stability of the obtained crystal structure when a same replica is used.

FIG. 9 is a graph illustrating the nitrogen adsorption-desorption isotherms of ICY-1, ICY-3, ICY-4 and ICY-2'. As seen from FIG. 9, all the nitrogen adsorption/desorption isotherms showed the hysteresis of the H2 type (the IV type in the IUPAC classification). This suggests that meso pores (pores having a diameter between 2 and 50 nm) existed and nitrogen adsorption attributable to capillary condensation took place under relative pressure of 0.5 to 0.8 in ICY-1, ICY-3, ICY-4 and ICY-2'. However, as described above by referring to FIG. 8, ICY-2' did not have any structure that is based on KIT-5 and hence seems to have meso pores that are structurally different from those of KIT-5.

The specific surface area, the pore capacity, the pore diameter. $D_1$ and the cage diameter $D_2$ of each of the ICYs were determined from the nitrogen adsorption-desorption isotherms. Table 2 shows the obtained results. As shown in Table 2, the specific surface area, the pore capacity, the pore diameter $D_1$ and the cage diameter $D_2$ of ICY-1, ICY-3 and ICY-4 were respectively $1,515 \text{ m}^2/\text{g}$, $2.0 \text{ cm}^3/\text{g}$, 5.2 nm and 15.0 nm, $1,600 \text{ m}^2/\text{g}$, $2.1 \text{ cm}^3/\text{g}$, 5.2 nm and 14.5 nm and $1,365 \text{ m}^2/\text{g}$, $1.8 \text{ cm}^3/\text{g}$, 5.6 nm and 14.0 nm. Particularly, it was found that ICY-3 had a specific surface area and a pore capacity that were the largest among the known carbon porous bodies.

From the above-described results, it became clear that, when a same replica is used, the ICY structure, particularly the specific surface area and the pore capacity thereof, can be changed by changing the mol ratio of the silicon (Si) in the silica porous body and the carbon (C) in the carbon source. More specifically, it became clear that both the specific surface area and the pore capacity decrease as the ratio of the carbon (C) in the carbon source to the silicon (Si) in the silica porous body increases. From the above, when KIT-5 is used, it is necessary for the mol ratio to satisfy requirement of $0.8 < C/Si < 3.0$, more preferably the requirement of $0.85 \leq C/Si \leq 0.95$.

TABLE 2

| Example | lattice constant $a_0$ (nm) | cane sugar/ KIT-5 mol ratio (C/Si) | specific surface area (m²/g) | Pore capacity (cm³/g) | pore diameter $D_1$ (nm) | cage diameter $D_2$ (nm) |
|---|---|---|---|---|---|---|
| Example 1 | 20.68 | 1.5 | 1515 | 2.0 | 5.2 | 15.0 |
| Example 2 | 18.2 | 1.5 | 1410 | 1.5 | 4.0 | 12.8 |
| Com. Ex 1 | 16.8 | 1.5 | 475 | 0.35 | — | 9.4 |
| Example 3 | 19.98 | 0.9 | 1600 | 2.10 | 5.2 | 14.5 |
| Example 4 | 19.48 | 2.4 | 1365 | 1.80 | 5.6 | 14.0 |
| Com. Ex 2 | 7.03 | 4.0 | 1125 | 1.47 | 5.8 | — |

Figure 10:
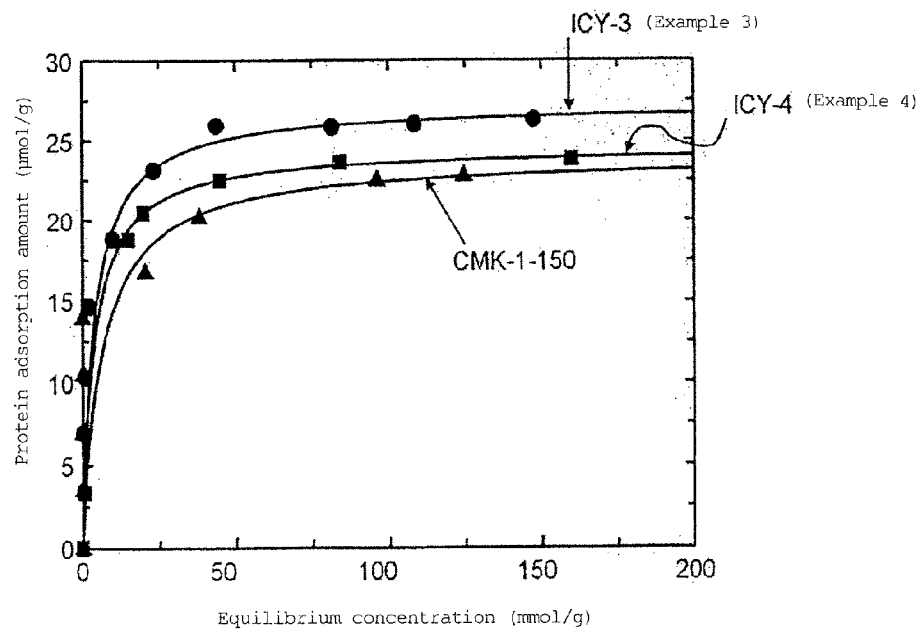
FIG. 10 is a graph illustrating the adsorption characteristics of the protein (lysozyme) of ICY-3, ICY-4 and CMK.

FIG. 10 is a graph illustrating the adsorption characteristics of the protein (lysozyme) of ICY-3 and ICY-4. Each of the adsorption characteristics agreed with the absorption isotherm expressed by formula (2) below.

$$n_s = Kn_m c/(1+Kc) \qquad (2)$$

In the formula (2), $n_s$ is the adsorption amount of lysozyme adsorbed to the carbon porous body and K is the Langmuir constant, while $n_m$ is the saturated adsorption amount of the mono-molecule layer and c is the lysozyme concentration. The saturated adsorption amounts of ICY-3 and ICY-4 as determined by means of the above formula (2) were respectively 26.5 μmol/g and 23.8 μmol/g. On the other hand, the saturated adsorption amount of the known CMK was 22.9 μmol/g.

The above-cited saturated adsorption amount of 26.5 μmol/g was higher than the highest value attainable by any known carbon porous body by more than 15%. Thus, from this fact, a carbon porous body showing a large pore capacity and a large specific surface area operates excellently for adsorption, collection, removal and fixation of biomolecules (proteins, nucleic acids and polysaccharides) having a large size.

Figure 11:
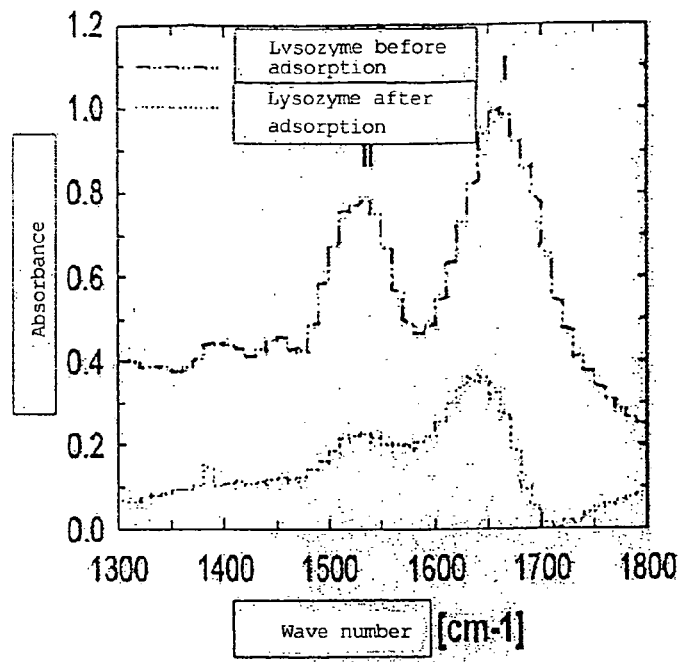
FIG. 11 is a graph illustrating the infrared absorption spectrum of a protein (lysozyme) observed before and after a protein (lysozyme) adsorption by ICY-3.
Figure 12:
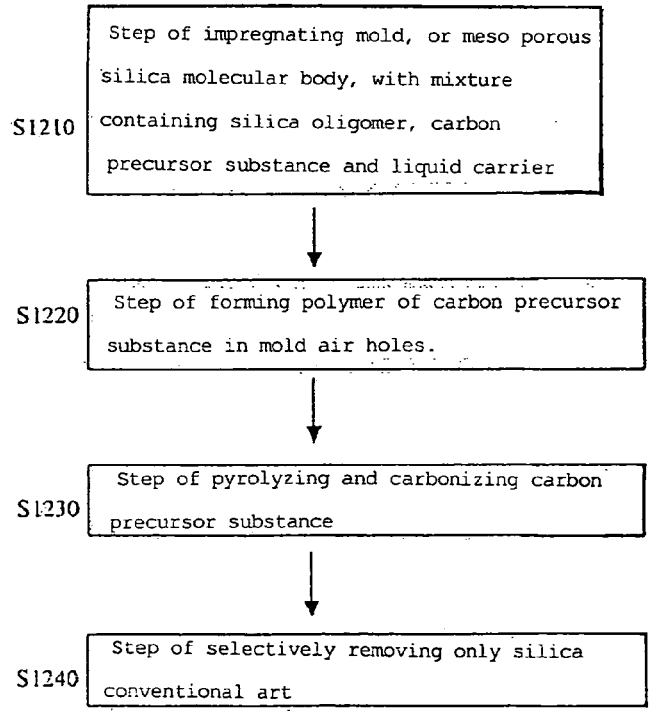
FIG. 12 is a flowchart of a known method of manufacturing a carbon molecular body.

FIG. 11 is a graph illustrating the infrared absorption spectrum of a protein (lysozyme) observed before and after a protein (lysozyme) adsorption by ICY-3. In FIG. 11, the dotted chain line indicates the infrared absorption spectrum of the lysozyme before the adsorption and the dotted line indicates the infrared absorption spectrum of the lysozyme after the adsorption by ICY-3. From FIG. 11, it was found that the infrared absorption spectrum of the lysozyme after the adsorption by ICY-3 was similar to that of the lysozyme before the adsorption. Besides, it was also found that the absorbance in the amide I and amide II bands did not change significantly before and after the adsorption. These facts suggest that the lysozyme adsorbed by ICY does not react with the ICY and hence is stable and that therefore the lysozyme adsorbed by ICY can find applications as a molecule recognition element for detecting a specific substance that reacts on the lysozyme. Additionally, fixed biomolecules maintains their stability after the fixation as described above and hence it is expected that such biomolecules can find applications in the field of reactors for digesting pollutants and sensors that are highly sensitive to harmful substances.

INDUSTRIAL APPLICABILITY

A manufacturing method according to the present invention employs a cage-shaped silica porous body where a plurality of pores is arranged three-dimensionally, regularly and symmetrically as replica. Since such a cage-shaped silica porous body has a specific surface area and a pore capacity smaller than those of any conventional replicas, the obtained carbon porous body can show a specific surface area and a pore capacity greater than ever. Then, such a cage-shaped silica porous body and a carbon source are mixed to a predetermined mol ratio (namely $0.8 < C/Si < 3.0$) and hence it is possible to obtain a carbon porous body that is free from conglutination of carbon and shows a high degree of regularity. The carbon porous body that is obtained in this way can show an improved adsorption effect than ever and adsorb large substances that conventional carbon porous bodies cannot. Additionally, the adsorbed substance can be dispersed into the inside of the carbon porous body with ease. Such a carbon porous body can find applications in the field of adsorbents, electrodes of fuel cells, sensors of molecule recognition elements and so on.

The invention claimed is:

1. A carbon porous body (ICY), comprising:
a carbon skeleton containing carbon atoms,
wherein the carbon skeleton includes carbon main sections and carbon linking sections mutually linking the carbon main sections,
a distance $D_1$ between adjacent carbon main sections and a distance $D_2$ between adjacent carbon linking sections satisfy a relationship of $D_1<D_2$, where $4 \leq D_1$ (nm) $\leq 6$ and $9 \leq D_2$ (nm) $\leq 15$,
the carbon main sections have a space group of Fm3m and are arranged three-dimensionally, regularly and symmetrically to form a face-centered cube,
a specific surface area of the carbon porous body is not less than 1,300 m$^2$/g and/or a pore capacity of the carbon porous body is not less than 1.5 cm$^3$/g, and
the carbon porous body is molded with a KIT-5 which is a cage-shaped silica porous body.

2. The carbon porous body according to claim 1, wherein the specific surface area of the carbon porous body is not less than 1,600 m$^2$/g and/or the pore capacity of the carbon porous body is not less than 2.0 cm$^3$/g.

3. An adsorbent, comprising:
a carbon porous body (ICY) including a carbon skeleton containing carbon atoms,
wherein the carbon skeleton includes carbon main sections and carbon linking sections mutually linking the carbon main sections,
a distance $D_1$ between adjacent carbon main sections and a distance $D_2$ between adjacent carbon linking sections satisfy a relationship of $D_1<D_2$, where $4 \leq D_1$ (nm) $\leq 6$ and $9 \leq D_2$ (nm) $\leq 15$,
the carbon main sections have a space group of Fm3m and are arranged three-dimensionally, regularly and symmetrically to form a face-centered cube,
a specific surface area of the carbon porous body is not less than 1,300 m$^2$/g and/or a pore capacity of the carbon porous body is not less than 1.5 cm$^3$/g, and
the carbon porous body is molded with a KIT-5 which is a cage-shaped silica porous body.

4. The adsorbent according to claim 3, wherein the specific surface area of the carbon porous body is not less than 1,600 m$^2$/g and/or the pore capacity of the carbon porous body is not less than 2.0 cm$^3$/g.

* * * * *